United States Patent [19]

Pardos

[11] 4,010,077
[45] Mar. 1, 1977

[54] BACTERIOLOGICAL TRANSFER LOOP

[76] Inventor: George Pardos, Whalers Point, East Haven, Conn. 06512

[22] Filed: Feb. 24, 1975

[21] Appl. No.: 552,213

[52] U.S. Cl. .................... 195/127; 195/120
[51] Int. Cl.$^2$ ............................. C12B 1/02
[58] Field of Search ............ 195/127, 120; 81/43, 81/3.48; 248/168, 169

[56] References Cited

UNITED STATES PATENTS

| 164,931 | 6/1875 | Page et al. ................ 81/3.48 |
| 2,204,013 | 6/1940 | Gaidos ...................... 248/168 |
| 2,212,013 | 8/1940 | Devareaux .................. 81/43 |
| 2,670,918 | 3/1954 | Kinnard ...................... 248/168 |
| 2,720,770 | 10/1955 | Bibeau ........................ 248/168 |
| 3,455,788 | 7/1969 | Curry et al. ................. 195/127 |
| 3,481,641 | 12/1969 | Berger et al. ............... 81/43 |

Primary Examiner—Alvin E. Tanenholtz
Attorney, Agent, or Firm—Arthur V. Smith; Pasquale A. Razzano

[57] ABSTRACT

A sterile disposable bacteriological transfer and inocculating loop has a base and a plurality of circumferentially spaced fingers extending generally in a common axial direction from the base and diverging from one another to free ends spaced further from one another than the portions of the fingers adjacent the base, whereby said fingers are adapted to be used successively to plate or streak a bacteriological specimen on a growth medium. Prior to use said fingers are enclosed in a cylindrical container which affords a sterile environment.

8 Claims, 10 Drawing Figures

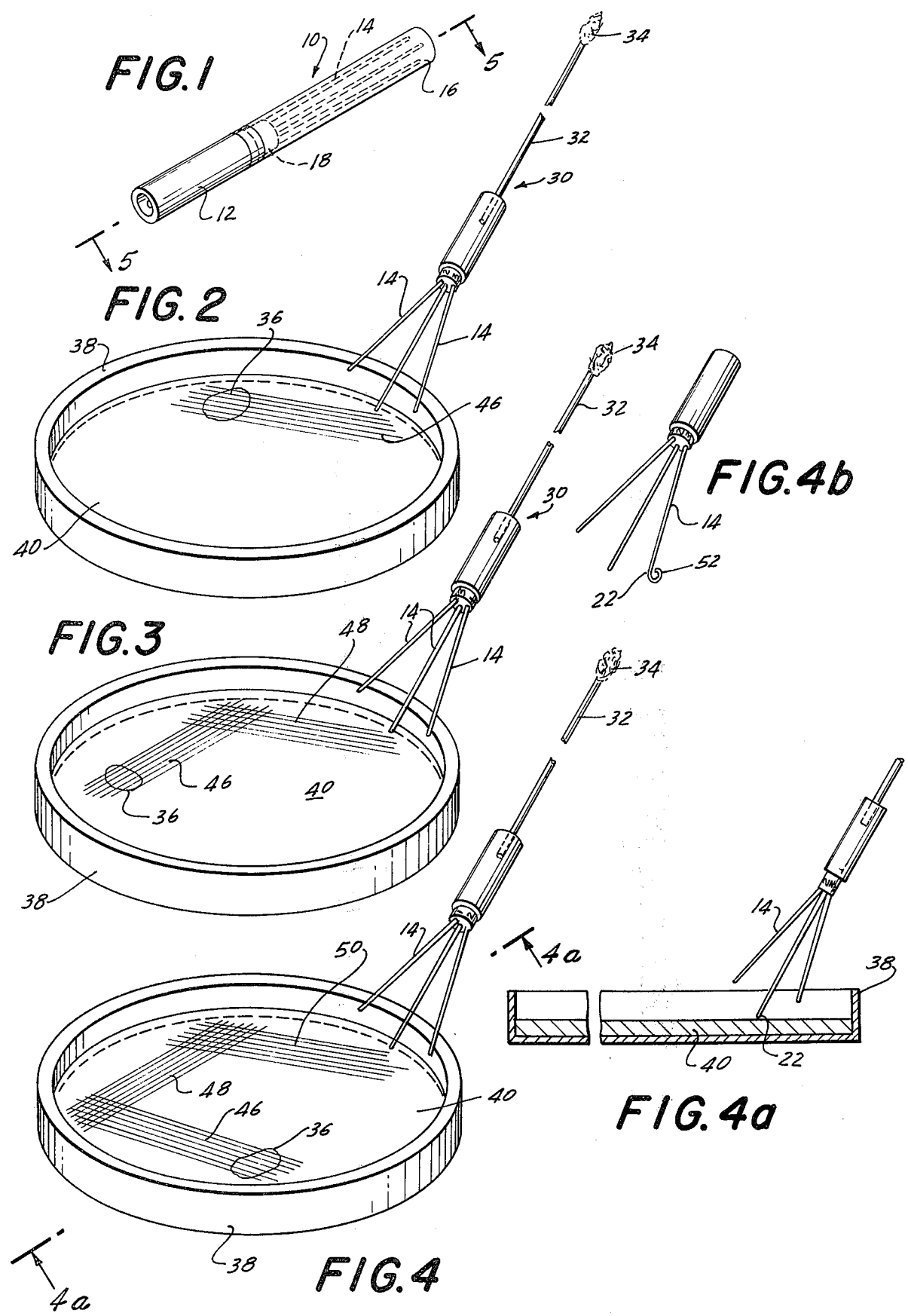

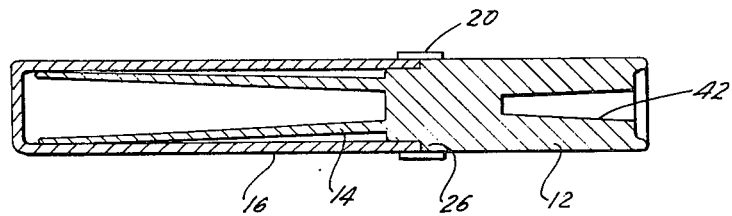
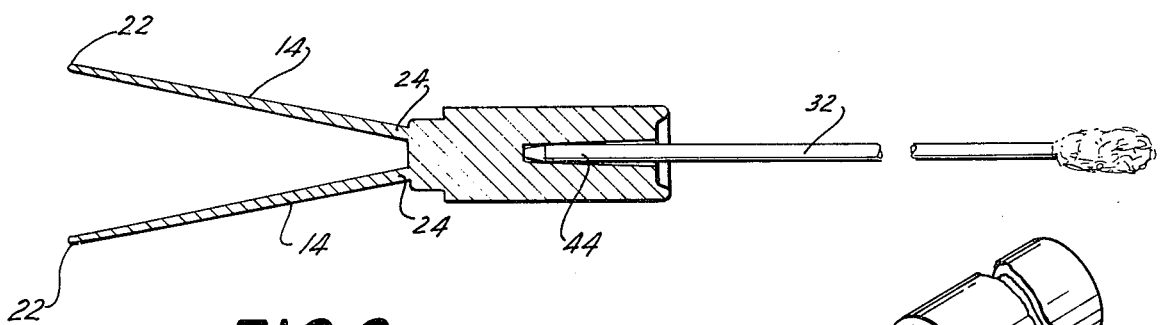
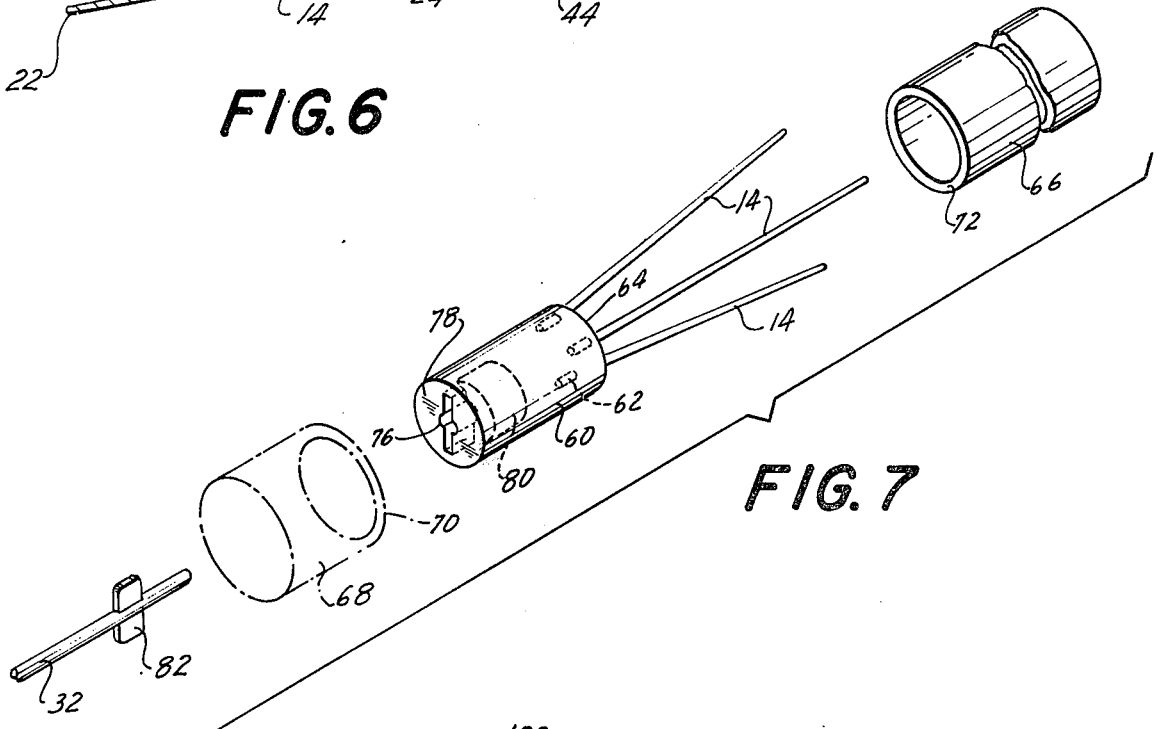
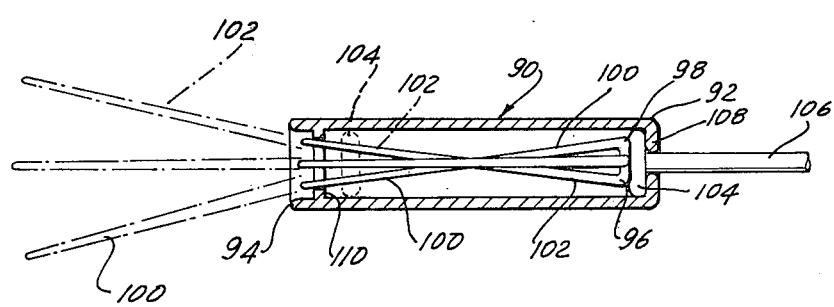

BACTERIOLOGICAL TRANSFER LOOP

The present invention relates to devices for use in bacteriological identification, and more particularly to an improved bacteriological transfer loop adapted to be used in streaking a specimen on a growth medium.

In the medical and biological arts it is common practice to culture or streak out bacteriological organisms on a solid growth medium in a Petri dish or the like in order to facilitate the study and identification of such organisms. This process is usually performed by placing a sample of the bacteria, which may have been derived from a specimen of a patient, in a discrete location on the growth medium by means of a loop or swab. Thereafter the specimen is streaked with the aid of a special wire loop in successive directions across the growth medium.

In a typical procedure the physician or technician will first streak the specimen in an initial direction along one side of the plate with the loop. He will then sterilize the loop over a Bunsen burner flame or the like, and continue streaking or spreading the specimen from the first streaked area across a second area. At that point he will again sterilize the loop and streak or spread the specimen from the second streaked area across a third area of the dish. Further streaking operations across the growth medium can be performed, with the streaking loop being sterilized between each separate streaking step. The purpose of the successive streaking steps is to progressively dilute the amount of bacteria on the loop or swab as it spreads the bacteria over each streaking area. This will sufficiently separate the individual bacteria in the specimen from one another, particularly in the last area streaked, so that visible colonies of growth result from each viable cell, with the colonies being spaced from one another to facilitate their study and identification.

Streaking out of a plate in this manner is a difficult and time consuming process, which requires a certain degree of skill and experience. It also requires extra equipment since the loop must be sterilized between each streaking step. Thus it normally is not possible for the physician to streak the bacteria on the growth medium as soon as the sample is taken from the patient. Accordingly, the usual procedure is for the physician to have the specimen sent to a special medical office or laboratory wherein a technician performs the streaking or plating operation. This of course adds to the time delay in obtaining an analysis of the bacteria and often is objectionable to the physician since the operation is not under his personal control.

Accordingly, it is an object of the present invention to provide a new and improved bacteriological transfer loop which will permit streaking or plating of a specimen on a growth medium by the physician without need for successive sterilization steps between successive streaking operations.

Another object of the present invention is to provide a pre-sterilized bacteriological transfer loop which can be used to perform a series of streaking operations without successive sterilization steps.

Yet another object of the present invention is to provide a bacteriological transfer loop which is simple in construction and economical in manufacture, so as to allow for its disposal after use.

A still further object of the present invention is to provide a bacteriological transfer loop which is durable in construction and adapted to be sterilized and maintained in a sterile condition prior to use.

In accordance with an aspect of the present invention the disposable bacteriological transfer and inoculating loop includes, in combination, a base having first and second opposite end portions with a plurality of circumferentially spaced fingers extending in a common generally axial direction from the first end portion of the base and preferably only in a single common circumferential row. The fingers are formed of a resilient material and diverge outwardly from one another along their length in a direction away from the base to free ends which are spaced further from one another than the portions of the fingers at the base. A hollow container is provided for receiving the fingers through an open end portion therein. The container cooperates with the base to enclose the fingers prior to use of the loop and the fingers diverge to their maximum extent upon removal from the container so that the fingers are individually available for use successively to plate or streak a bacteriological specimen on the growth medium. The container provides a sterile chamber for the fingers during storage, so that the individual fingers, upon removal from the container, are in a sterile condition and each individual finger can be successively used in successive streaking operations. Accordingly the physician can carry the loop with him and perform the streaking operation at the patient's bedside without any need to sterilize the loop between successive streaking steps in the procedure.

The above, and other objects, features and advantages of the present invention will be apparent to those skilled in the art from the following detailed description of illustrative embodiments thereof which are to be read in connection with the accompanying drawings therein:

FIG. 1 is a perspective view of a bacteriological loop constructed in accordance with the present invention and held within its sterile container;

FIGS. 2–3 are perspective views illustrating the use of the bacteriological loop in the performance of three successive streaking operations;

FIG. 4a is an elevational view, in section, taken along line 4A—4a in FIG. 4;

FIG. 4b is a perspective view of a bacteriological loop constructed in accordance with another embodiment of the present invention;

FIG. 5 is a sectional view taken along line 5—5 of FIG. 1;

FIG. 6 is a sectional view, similar to FIG. 5, of the bacteriological loop when removed from its sterile container and having a manipulating rod mounted therein;

FIG. 7 is an exploded perspective view of another embodiment of the present invention; and FIG. 8 is a sectional view, similar to FIG. 5, of a still further embodiment of the invention.

Referring now to the drawing in detail, and initially to FIG. 1 thereof, it will be seen that a bacteriological transfer loop 10, constructed in accordance with the present invention, includes a main base or body member 12 from which a plurality of individual fingers 14 extend. The fingers are retained in a generally cylindrical hollow container or cover 16 having an open end 18 (not seen in FIG. 1) through which the fingers are received and which engages the base 12. A strip of adhesive tape 20 provides a secure and substantially vapor tight seal between the end 18 of the container 16 and the base 12.

In accordance with one embodiment of the present invention, as illustrated in FIG. 5, the base 12 and fingers 14 can be formed of a one piece molded plastic construction, with the fingers being resilient and diverging from one another. Thus, upon removal of cover 16, fingers 14 will move outwardly into the position shown in FIG. 6. As seen therein, the individual fingers 14 extend generally in the same axial direction, but diverge slightly from one another so that their free ends 22 are further from one another than their bases 24. In addition, it is noted that the individual fingers are circumferentially spaced from one another at their bases 24 in a single circumferential row.

Although fingers 14 have been described as being integrally formed with base 12, it is contemplated that the fingers may be separately formed from the base and in fact can be metal rods or the like inserted or mounted in base 12 in any convenient manner so long as they diverge slightly from one another. In either case the fingers are slightly rounded or shaped at their free ends 22 so as not to cut or damage the growth medium when used.

Preferably, the inoculating loop 10 is packaged as illustrated in FIG. 5, with the container 16 surrounding the fingers 14 and engaged with a shouldered portion 26 of the base. The tape 20 surrounds the joint between the base and the cover and forms a vapor tight seal as described above. With the package assembled in this manner the device can be sterilized in an autoclave or in a sterile atmosphere, as would be understood by those skilled in the art, with the tape 20 serving to maintain a vapor tight seal while the device is in storage. In this manner the sterility of the fingers 14 is retained.

When it is desired to perform a streaking or plating operation, the physician takes a specimen from the patient, in the conventional manner. This is usually done with a cotton swab 30, which consists of a rod 32 and a swab tip 34. The specimen on the swab tip 34 is then applied to a small area 36 on the growth medium in a Petri dish 38 or the like.

As illustrated in FIGS. 2-4 Petri dish 38 is of conventional construction and contains a conventional gel like growth medium such as agar or agrose. Once the specimen is applied the physician then uses loop 10 to streak the specimen and thus progressively dilute the amount of bacteria along the surface of the growth medium 40. To do this the physician or technician removes the adhesive strip 20 from the device and removes the loop from container 16. This allows the fingers 14 to spread apart, into the configuration illustrated in FIG. 6. The physician can then use the loop by grasping the base 12 thereof between his fingers or, alternatively, the rod 32 of the swab can be used as a handle.

In the illustrative embodiment of the invention the base 12 of the device has a generally conically shaped recess 42 formed therein which is adapted to frictionally engage the end 44 of the swab 32. The physician can then use the rod as a handle in order to manipulate the loop.

In any case, when the streaking operation is to be performed one of the fingers 14 is placed on the growth medium 40 and moved across the specimen 36 to form a series of streak lines 46 across a portion of the growth medium, thereby spreading or streaking the specimen in a first area. The loop or device 10 is then rotated to present a second finger to the growth medium and the streaking procedure is repeated, by moving the finger across the previously streaked lines 46 to form a second set of streak lines 48. In this manner the bacteria in a portion of the lines 46 are transferred to the streak lines 48 and their concentration is diluted. To further dilute the bacteria the physician or technician rotates the device 10 to present the third finger to the growth medium and forms a third set of streak lines 50 on the growth medium further spreading and diluting the bacteria.

In order to facilitate the identification of the respective fingers, to assure that no finger is used twice in the streaking operation, the base 12 can be provided with indicia thereon adjacent the base of each of the fingers 14 to distinguish the fingers from one another. Thus in the first streaking step shown in FIG. 2 the physician would use the finger identified as number 1 while in the second and third streaking steps the physician would use the fingers identified as 2 and 3 respectively.

In this manner, the streaking operation can be performed immediately by the physician without the need to sterilize each of the individual fingers prior to use. This represents a substantial savings in time as compared to previously proposed streaking operations where an individual loop is used which must be sterilized over a Bunsen burner between each streaking step. Moreover, since the device can be made of relatively inexpensive plastic materials, it can be disposed of immediately after use; whereas with previously proposed inoculating or streaking loops, the loops are formed of precious metals and therefore would not be disposable.

As illustrated in FIG. 4a during the streaking operation only the tip 22 of one of the fingers contacts the growth medium 40. The other two fingers, because of their diverging and circumferentially spaced relationship to one another, will remain spaced from the surface of the growth medium as the loop is reciprocated in the streaking process.

Another embodiment of the invention is illustrated in FIG. 4b wherein one of the fingers 14 is provided with a curved loop 52 formed at its free end 22. This loop preferably has a calibrated or predetermined diameter or area so that it can be used to apply a predetermined amount of a liquid specimen to the growth medium. For example, where bacteria in a urine sample is to be studied, the physician can use the looped finger 14 of the embodiment in FIG. 4b to collect a predetermined amount of urine from a specimen by dipping the loop 52 into the specimen so as to form a thin film in the loop area. As a result a predetermined amount of the urine specimen would form the film in the loop. The physician can then tap the loop gently on the surface of the growth medium to deposit the liquid film thereon in the area 36. The loop 52 could then be used in the conventional manner to perform the first streaking step or set of lines 46 and the other two fingers would then be used successively, as previously described, to further spread, streak and dilute the bacteria in the specimen. Again, this arrangement avoids the need for sterilizing the loop between successive streaking operations.

Another embodiment of the present invention is illustrated in FIG. 7. In this embodiment a base 60, similar to the base 12 previously described is provided in which a plurality of fingers 14 are mounted. The fingers can be formed of a separate material such as metal or the like with their inner ends 62 received in recesses in the end 64 of the base. The fingers can be secured in the recesses in any convenient manner, as for example by a suitable adhesive.

A container 66 also is provided for receiving and enclosing the fingers 14 of this embodiment. In addition, a cap or cover 68 can be provided for fully enclosing the base 60 of this device. The free end 70 of this cover 68 mates with and engages the free end 72 of cover 66 and a strip of adhesive tape (not shown) can be used to seal the two elements together and fully enclose the loop device within a sterile chamber.

In this embodiment of the invention another form for attaching the handle or manipulating rod to the base 60 of the device is illustrated. As seen therein a keyhole slot 76 can be provided in the rear end 78 of the base, providing access to an interior chamber 80 therein. The swab rod 32 in this case can be provided with a pair of projections 82, which may be preformed on the rod or can simply be formed by the physician by squeezing the rod prior to insertion in the base 60. In any case, the projections 82 will pass through the keyhole slot 76, into the recess 80. Upon rotation of the rod 32 through 90°, removal of the rod will be prevented and a firm handle will be provided for the base 60. Thereafter the loop device of FIG. 7 is used in the same manner as the loop devices described above.

Yet another embodiment of the invention is illustrated in FIG. 8 of the drawing. The device 90 of FIG. 8 includes a hollow cylindrical container 92 having a first open end portion 94. A plurality of U-shaped elements 96 formed of a resilient material such as plastic or metal, are integrally connected at their bight portions 98 and are formed so that their legs 100, 102 normally cross each other in their unstressed condition. The bight portions 98 of these fingers are engaged by a push member 104 having an integral handle 106 extending through the rear end 108 of container 92.

An internal annular flange 110 is provided within the cylinder 92 adjacent the open end 94 thereof. This cylinder will engage the rear end portions of the fingers 102 as the fingers are urged outwardly by the push rod 106 (i.e. when moved in the left direction of FIG. 8) so as to cause the fingers to diverge further from one another. As a result, when the fingers are fully exposed and the push member 104 reaches the dotted line position thereof in FIG. 8 the fingers 100, 102 of the various U-shaped finger members will assume their dotted line position. Prior to use the open end 94 is sealed to insure sterility or the entire embodiment is enclosed in a sterile envelope.

In this embodiment, although the handle 106 has been described as being integrally formed with the push member 104 it will be appreciated that the handle 106 need not be integrally formed and in fact could simply be the end of the swab 32 as previously described.

Accordingly, it is seen that relatively simply constructed transfer loop devices have been provided which are durable in use and inexpensive to manufacture. The devices have the highly beneficial advantage that they need not be sterilized during the streaking process; as a result they save the physician or technician a substantial amount of time previously consumed in sterilization procedures. Moreover, because the devices are relatively inexpensive to produce and manufacture, they can be disposed of after a single use.

Although illustrative embodiments of the present invention have been described herein with reference to the accompanying drawings, it is to be understood that the invention is not limited to those precise embodiments and that various changes and modifications may be effected therein by one skilled in the art without departing from the scope or spirit of this invention.

What is claimed is:

1. A disposable bacteriological transfer and inoculating loop comprising a base and a plurality of circumferentially spaced fingers extending generally in a common axial direction from said base and diverging from one another to free ends spaced further from one another than the portions of the fingers adjacent said base, whereby said fingers are adapted to be used successively to plate or streak a bacteriological specimen on a growth medium; means in said base opposite said fingers for removably securing an elongated rod to said base whereby said rod may serve as a manipulating handle for said loop; said rod having an enlargement formed at one end thereof and said means comprising a keyhole type slot in said base adapted to receive said one end of said rod and a recess formed in the base behind the slot to receive said enlargement when the rod is inserted in the slot whereby rotation of the rod in said slot will cause the base to be positively secured to said one end of the rod.

2. A disposable bacteriological transfer and inoculating loop comprising a base and a plurality of circumferentially spaced fingers extending generally in a common axial direction from said base and diverging from one another to free ends spaced further from one another than the portion of the fingers adjacent said base, whereby said fingers are adapted to be used successively to plate or streak a bacteriological specimen on a growth medium; at least one of said fingers having a generally circular loop of predetermined dimensions formed at one end thereof for applying a calibrated amount of a bacteriological specimen to a growth medium.

3. A disposable bacteriological transfer and inoculating loop comprising a base and a plurality of circumferentially spaced fingers rigidly secured to said base in spaced relation to each other, and extending generally in a common axial direction from said base and diverging from one another to straight free working end portions spaced further from one another than the portions of the fingers adjacent said base, whereby said fingers are adapted to be used successively to plate or streak a bacteriological specimen on a growth medium; said free working end portions of the fingers having rounded ends to avoid damaging the growth medium during streaking and said base being a generally hollow cylinder; said fingers comprising resilient members received in said cyclinder; and said cylinder including means for pushing said fingers outwardly of said cylinder and means for spreading said fingers, as they are urged out of the cylinder, into said diverging relation with respect to one another.

4. A disposable bacteriological transfer and inoculating loop comprising a base and a plurality of circumferentially spaced resilient fingers rigidly secured to said base in spaced relation to each other, and extending generally in a common axial direction from said base and diverging from one another to straight free working end portions spaced further from one another than the portions of the fingers adjacent said base, whereby said fingers are adapted to be used successively to plate or streak a bacteriological specimen on a growth medium; said free working end portions of the fingers having rounded ends to avoid damaging the growth medium during streaking; and a hollow container having one open end through which said fingers are received, said container cooperating with said base to enclose said fingers prior to use of the loop, and means for sealing said container to said base in a substantially vapor tight seal to prevent contamination of the fingers prior to use.

5. A disposable bacteriological transfer and inoculating loop comprising, in combination, a base having first and second opposite end portions and a plurality of circumferentially spaced fingers secured to said base in spaced relation to each other and extending in a common generally axial direction from said first end portion of the base; said fingers being formed of a resilient material and diverging outwardly from one another along their length in a direction away from said base to straight free working end portions; and a hollow container for said fingers having an open end portion through which said fingers are received; said container cooperating with said base to enclose said fingers prior to use of the loop, said resilient fingers diverging to their maximum extent upon removal of said container from about said fingers whereby said fingers are available for use successively to plate or streak a bacteriological specimen on a growth medium; said free working end portions of the fingers having rounded ends to avoid damaging the growth medium during streaking.

6. The device as defined in claim 5 including means for forming a removable substantially vapor tight seal between said base and said container whereby said fingers can be maintained in a sterilized condition in the container prior to use in a streaking operation.

7. The device as defined in claim 6 including means in said base opposite said fingers for removably securing an elongated rod to said base whereby said rod may serve as a manipulating handle for said loop.

8. The device as defined in claim 7 wherein said fingers are formed of a resilient material.

* * * * *